United States Patent [19]

Fedorov et al.

[11] Patent Number: 4,863,462

[45] Date of Patent: Sep. 5, 1989

[54] POSTERIOR-CHAMBER INTRAOCULAR PROSTHETIC LENS

[75] Inventors: Svyatoslav N. Fedorov; Nadezhda F. Pashinova; Sergei I. Anisimov; Evgeny I. Degtev; Dmitry V. Zakharov; Alexandr A. Karavaev; Vladimir G. Kiselev, all of Moscow; July A. Juzhelevsky; Sergei V. Sokolov, both of Leningrad, all of U.S.S.R.

[73] Assignee: Mezhotraslevoi Nauchno-Tekhnichesky Komplex "Mikrokhirurgii Glaza", Moscow, U.S.S.R.

[21] Appl. No.: 240,125

[22] PCT Filed: Oct. 29, 1986

[86] PCT No.: PCT/SU86/00109

§ 371 Date: Jun. 8, 1988

§ 102(e) Date: Jun. 8, 1988

[87] PCT Pub. No.: WO88/03009

PCT Pub. Date: May 5, 1988

[51] Int. Cl.[4] .............................................. A61F 2/16
[52] U.S. Cl. ....................................................... 623/6
[58] Field of Search ............................................ 623/6

[56] References Cited

U.S. PATENT DOCUMENTS

| 4,092,743 | 6/1978 | Kelman | 623/6 |
| 4,159,546 | 7/1979 | Shearing | 623/6 |
| 4,418,431 | 12/1983 | Feaster | 423/6 |
| 4,588,405 | 5/1986 | Knolle, Jr. | 623/6 |
| 4,601,721 | 7/1986 | Kamerling | 623/6 |
| 4,610,689 | 9/1986 | Greather | 623/6 |

OTHER PUBLICATIONS

The Journal of The American Academy of Opthalmology, pp. 128–130, (Vol. 89, No. 8S, August Supplement, 1982).

Primary Examiner—Ronald L. Frinks
Attorney, Agent, or Firm—Fleit, Jacobson, Cohn, Price, Holman & Stern

[57] ABSTRACT

A posterior-chamber intraocular prosthetic lens includes an optical lens (1) and two diametrically opposite supporting elements (2), each of the supporting elements (2) being shaped as a curvilinear body one of its lateral surfaces being convex and facing with its convex portion (3) in a direction opposite to the lens principal plane, while the other lateral surface of the body is cancave and faces with its concave portion (4) toward the lens (1) principal plane; the ends of the supporting elements (2) are rounded off and face each other, while the supporting elements (2) are spatially turned away from each other with respect to the principal plane of the optical lens.

1 Claim, 2 Drawing Sheets

POSTERIOR-CHAMBER INTRAOCULAR PROSTHETIC LENS

This application claims priority from International Application PCT/SU86/00109, filed Oct. 29, 1986.

FIELD OF THE INVENTION

This invention relates to prosthetic devices and to means for their attachment to the human body and more specifically it concerns posterior-chamber intraocular prosthetic lenses.

PRIOR ART

It is common knowledge that surgical treatment of various eye diseases is not infrequently encountered with a necessity for removal of the crystalline lens followed by its substitution by a prosthetic lens or lenticulus, otherwise called intraocular lens. As a rule, the process of implantation of the prosthetic lenses into the posterior eye chamber is impeded due to such complications as rupture of the posterior lenticular capsule and vitreoptosis.

Known in the present state of the art is an intraocular lens by Shearing (cf, the Journal of the American Academy of the Ophthalmology, 1982, V.89, No. 8S, p. 128), comprising an optical lens and two diametrically opposite supporting elements that lie in a plane coplanar with the lens principal plane. However, said intraocular lens is difficult to implant, since insertion of the supporting elements in the slitlike posterior eye chamber is frequently liable to result in formation of folds of the posterior chamber, which in turn lead to rupture of the posterior lenticular capsule in the course of implantation. Thus, eye irrigation has to be resorted to. This, consequently prolongs the operating time, renders the surgical procedure less convenient, and contributes to a greater amount of corneal edema resulting from the effect of the irrigation fluid on the eye being treated. All this extends the postoperative treatment of the patients operated upon. Moreover, the aforementioned arrangement of the supporting elements fails to prevent the implanted intraocular lens from dislocation within the postoperative period.

Another intraocular lens by Pierce (cf. The Journal of the American Academy of Opthalmology, 1982, V.89, No. 8S, p. 130) comprises an optical lens and three radially arranged supporting elements coplanar with the lens principal plane. The intraocular lens is also to be inserted in the posterior eye chamber. To this end, the lens is introduced with one of its supporting elements into the posterior eye chamber, while the other two supporting elements are inserted by displacing the iris and putting over said elements. Such a procedure is also accompanied rather frequently by rupture of the posterior capsule, since when implanted in the posterior eye chamber, the flat supporting element moves towards the posterior lenticular capsule with an edge at a certain angle thereto. Thus, the edge of the supporting elements rests against the capsule and might injure the latter when being moved further on. Besides, arrangement of the supporting elements coplanarly with the lens principal plane results in the lens being liable to dislocate with respect to the visual axis rather frequently, thus affecting eyesight adversely. Furthermore, reliably holding of the intraocular lens needs application of an additional suture fixing the lens to the iris. This extends the operating time and renders the surgical procedure more traumatic which, eventually, results in a longer postoperative period of patients' rehabilitation.

ESSENCE OF THE INVENTION

It is a primary and essential object of the invention to provide a posterior-chamber intraocular prosthetic lens, wherein the shape of supporting elements would prevent postoperative complications.

Said object is accomplished due to the fact that in a posterior-chamber intraocular prosthetic lens, comprising an optical lens and at least two diametrically opposite supporting elements, according to the invention, each of the supporting elements is in fact a curvilinearly shaped body, one of its lateral surfaces being convex and facing with its convex portion oppositely with respect to the lens principal plane, and the other lateral surface of said body is concave and faces with its concave portion towards the lens principal plane, the ends of the supporting elements are rounded off and face each other, the supporting elements themselves being turned away from each other with respect to the lens principal plane.

The herein-proposed construction of a posterior-chamber intraocular prosthetic lens offers quite a number of substantial advantages which are the subject of a brief consideration that follows hereinbelow.

Provision in the intraoccular lens in question of at least two supporting elements, each shaped as a curvilinear body with one of its lateral surfaces being convex makes it possible to fix the lens in the posterior chamber or in the lenticular capsule. In this case the convex surfaces facing oppositely with respect to the lens principal plane, make part of the intraocular prosthetic lens that is in contact with the ocular tissues.

Provision of the concave surfaces in the supporting elements makes it possible to minimize traumatic lesion inflicted by the present posterior-chamber intraocular prosthetic lens upon the iris, this being due to a reduced contact area of the iris and the supporting elements, since the supporting element, after having been implanted in the patient's eye, tends to set "edgewise". It is just at that instant that the provision of a concave surface enables one to avoid the injuring effect of the edge of the prosthetic edge upon the adjacent tissues. Turning of the supporting elements away from each other with respect to the principal plane passing through the lens optical centre, makes it possible to enlarge the slitlike space in the posterior chamber at the instant of the lens implantation due to rotation of the lens in the horizontal plane. This makes it possible to introduce the supporting elements into the posterior eye chamber unobstructedly without resorting to irrigation. Such a spreading of the posterior iridal surface and the posterior lenticular capsule by the supporting elements turned spatially during implantation reduces the amount of ruptures of the posterior lenticular lens during this stage of implantation, accompanied by vitreoptosis, simplifies the implantation procedure and cuts down the operating time. In addition, said spatial turning of the supporting elements makes it possible for the intraoccular lens to rest, with the lateral edges of the supporting elements, against the lenticular capsule, which increases the reliability of its fixation, thus rendering the danger of the lens getting off-centre less possible. The fact that the ends of the supporting elements face each other and are rounded off is necessary in order that the spatially turned out supporting elements should not injure the endothelial corneal layer in the course of implantation and should prevent the lens from rotation in the posterior eye chamber when inserting the supporting elements.

SUMMARY OF THE DRAWINGS

Other advantages and specific features of the present invention will become apparent from a consideration of an embodiment thereof described hereinbelow by way of example with reference to the accompanying drawings, wherein.

PREFERRED EMBODIMENT OF THE INVENTION

Figure 1:
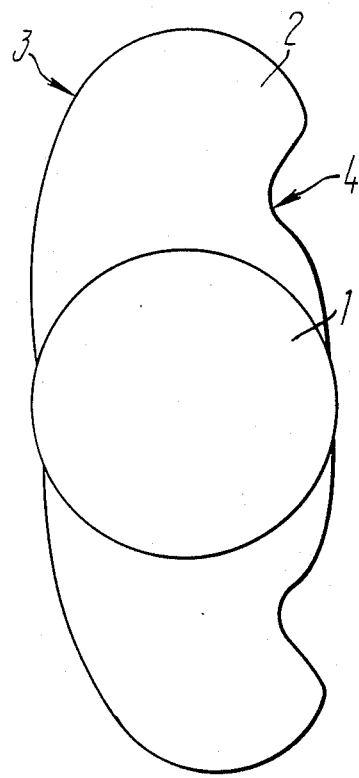
FIG. 1 is a general schematic view of a posterior-chamber intraocular prosthetic lens, according to the invention.
Figure 2:
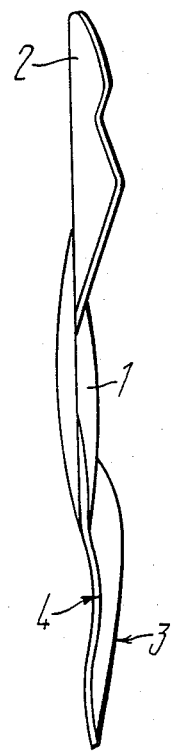
FIG. 2 is a side view of FIG. 1, according to the invention.
Figure 3:
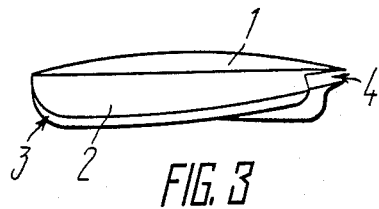
FIG. 3 is a plan view of FIG. 1, according to the invention.

A posterior-chamber intraocular prosthetic lens of the invention comprises an optical lens 1 (FIG. 1) and two diametrically opposite supporting elements 2, each of the supporting elements 2 being in fact a curvilinearly shaped body. One of the lateral surfaces of the aforesaid body is convex and faces, with its convex portion 3 in a direction opposite to the principal plane of the lens 1, while the other lateral surface of said body is concave and faces with a concave portion 4 towards the principal plane of the lens 1. The ends of the supporting elements 2 are rounded off and face towards each other, while the supporting elements 2 are spatially turned away from each other with respect to the principal plane passing through the optical centre of the optical lens 1 as can be seen from FIGS. 2 and 3.

The aforediscussed posterior-chamber intraocular prosthetic lens can be manufactured by casting from a special elastic material.

Figure 4:
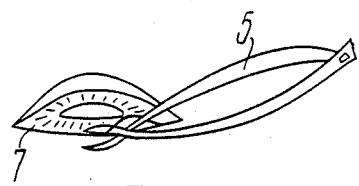
FIGS. 4 through 10 represent the stages of the implantation of a posterior-chamber intraocular prosthetic lens, according to the invention.
Figure 8:
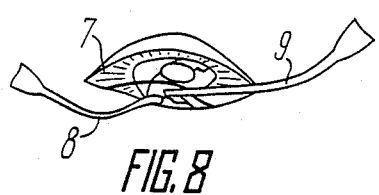
Figure 5:
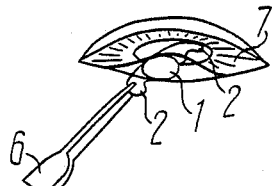
Figure 9:
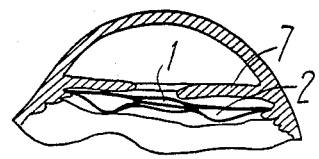
Figure 6:
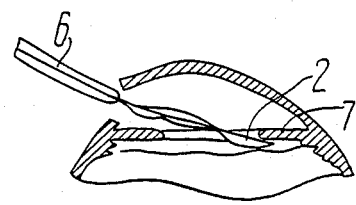
Figure 10:
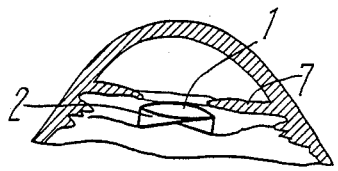
Figure 7:
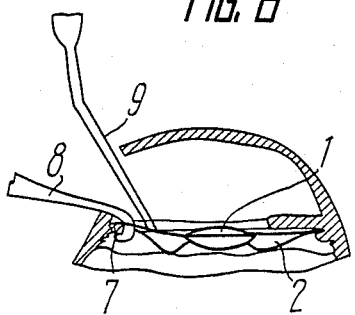

Implantation of a posterior-chamber intraocular prosthetic lens is carried out in an order shown in FIGS. 4 through 8. A 3-mm long corneoscleral incision is made with a scissors 5, under local anesthesia, along the 17 o'clock meridian, whereupon the irrigation system is brought through said incision. Next a 4 to 6-mm long limbal incision is made from 11 to 14 o'clock (FIG. 4). The anterior lenticular capsule is slit open in a routine way adopted in extracapsular cataract extraction. The nucleus and lenticular masses are also extracted typically of an extracapsular cataract extraction. Thereupon the intraocular lens is caught by one of its supporting elements 2 with a forceps 6 (FIGS. 5, 6) and is brought, with the free supporting element 2, into the posterior eye chamber (omitted in the drawing). Next the optical lens 1 is turned in a horizontal plane, the supporting element 2 located in the pupillar opening is also turned in a horizontal plane and dislodges the posterior surface of the iris 7 from the lenticular capsule, whereby that supporting element 2 can be introduced freely and completely into the posterior eye chamber. Thereupon the superior portion of the iris 7 (FIG. 7) is pulled back by an iridoretractor 8, and the supporting element 2 is invaginated, with a spatula 9 (FIG. 8) into the posterior eye chamber, with the result that the intraocular lens assumes a horizontal position in said chamber (FIGS. 9, 10).

It is a curvilinear shape of the supporting elements 2 and provision of the concave surface 4 that minimize traumatic lesion inflicted upon the iris 7 in the course of implantation of the present intraocular prosthetic lens, this being due to a reduced contact area between the iris 7 and the supporting elements 2, since the supporting element 2 that has been implanted in the posterior eye chamber first tends to turn to get parallel to the iris 7, thus causing the other supporting element 2 located in the anterior eye chamber to turn on its lateral surface.

The fact that the supporting elements are spatially turned away from each other with respect to the lens principal plane provides for unobstructed insertion of the present posterior-chamber intraocular prosthetic lens in the posterior eye chamber. This is attained due to spreading the posterior iridal surface and the posterior lenticular capsule by the turned out supporting elements, which reduces the amount of ruptures of the posterior lenticular capsule accompanied by vitreoptosis, at the instant of implantation of the present intraocular lens in the posterior eye chamber. The fact that the ends of the supporting elements face each other and are rounded off is necessary in order that the spatially turned out supporting elements should not injure the endothelial corneal layer and should prevent the lens from rotation in the posterior eye chamber during implantation.

Given below are some exemplary case histories.

Male patient M., 64, was admitted to the clinic with a diagnosis of senile cataract of the right eye. Visual acuity on admission: OD—correct light projection; OS—0.9 not corrected.

The patient was operated upon for extracapsular cataract extraction with implantation of a posterior-chamber intraocular prosthetic lens +24.0 D on the right eye.

The surgery and postoperative period uneventful. The patient was dismissed in three days after the operation.

Visual acuity on dismissal: OD—1.0 without correction; OS—0.9 not corrected.

Female patient V., 45, was admitted to the clinic with a diagnosis of complicated cataract of the left eye. Visual acuity on admission: OD—1.0; OS—0.01 not corrected.

The patient was operated upon for extracapsular cataract extraction with implantation of a posterior-chamber intraocular prosthetic lens in the left eye. The surgery and postoperative period uneventful.

The patient was dismissed in five days after surgery. Visual acuity on dismissal: OD—1.0; OS—1.0 without correction.

The proposed posterior-chamber intraoccular prosthetic lens is useful intraocular correction of aphakia following cataract extraction of any etiology.

INDUSTRIAL APPLICABILITY

The invention can find application in opthalmological practice for intraocular eyesight correction following the extraction of a cataract of any etiology.

We claim:

1. A posterior-chamber intraocular prosthetic lens comprising
    an optical lens, at least two diametrically opposite supporting elements connected to opposite sides of the optical lens, each of the supporting elements is a curvilinearly shaped body, one of the lateral surfaces of the bodies of the supporting elements being convex and facing with its convex portion in a same direction opposite to a principal plane of the optical lens, while the other lateral surface of the bodies of the supporting elements is concave and faces with its concave portion in a same direction towards the principal plane of the optical lens ends of the supporting elements are rounded off and face each other, while the supporting elements are spatially turned away from each other with respect to the lens principal plane.

* * * * *